(12) United States Patent
Chen et al.

(10) Patent No.: US 7,501,095 B2
(45) Date of Patent: Mar. 10, 2009

(54) APPARATUS FOR ON-LINE SAMPLING OF METAL NANOPARTICLE FLUID AND TECHNIQUE OF THE SAME

(75) Inventors: Liang-Chia Chen, Jhonghe (TW); Tshih Tsung, Taipei (TW); Jen-Yan Sun, Jhudong Township, Hsinchu County (TW); Hong-Ming Lin, Taipei (TW)

(73) Assignee: National Taipei University of Technology, Taipei (TW)

( * ) Notice: Subject to any disclaimer, the term of this patent is extended or adjusted under 35 U.S.C. 154(b) by 1016 days.

(21) Appl. No.: 10/771,425

(22) Filed: Feb. 5, 2004

(65) Prior Publication Data
US 2005/0002829 A1 Jan. 6, 2005

(30) Foreign Application Priority Data
Jul. 4, 2003 (TW) .............................. 92118404 A

(51) Int. Cl.
*B01L 3/02* (2006.01)
(52) U.S. Cl. ........................... 422/100; 422/99; 75/331; 436/180; 977/700; 977/963
(58) Field of Classification Search ........... 422/99–100; 75/331; 436/180; 977/700, 963
See application file for complete search history.

(56) References Cited

U.S. PATENT DOCUMENTS
5,569,844 A 10/1996 Sowerby

FOREIGN PATENT DOCUMENTS
| TW | 120030 | 10/1989 |
| TW | 248309 | 5/1995 |
| TW | 434067 | 5/2001 |
| TW | 506867 | 10/2002 |

*Primary Examiner*—Jill Warden
*Assistant Examiner*—Jyoti Nagpaul
(74) *Attorney, Agent, or Firm*—Rabin & Berdo, P.C.

(57) ABSTRACT

The invention provides an on-line sampling apparatus for the metal nanoparticle fluid of the vacuum submerged arc process and the method thereof, using the principle of the pressure difference between the vacuum pump and the vacuum chamber and the constant temperature design of the sample pipeline to make the sample precisely be caught and flow into the predetermined collector, and the disadvantage of the vaporization of the sample due to the temperature rise caused by the ambient temperature can be prevented. Further, the invention integrates with a particle size analysis apparatus to carry out real time measurement and data analysis of the nanoparticle fluid with real time process characteristics, wherein the nanoparticle fluid is caught from the nanofluid process line, thus, the optimal design work of the process and the system parameters and particle quality monitoring may be proceeded efficiently.

21 Claims, 4 Drawing Sheets

APPARATUS FOR ON-LINE SAMPLING OF METAL NANOPARTICLE FLUID AND TECHNIQUE OF THE SAME

FIELD OF THE INVENTION

The invention generally relates to an on-line sampling technique for a metal nanoparticle fluid, and especially to the on-line sampling apparatus and a sampling method for the metal nanoparticle fluid, which can be used to online catch the nanoparticle fluid with real time processing characteristics as the sample and is applicable to a manufacture equipment used to produce the metal nanoparticle fluid in low temperature and under negative pressure.

BACKGROUND OF THE INVENTION

Accordingly, the present vacuum submerged arc production method and machine thereof as a heat source are to provide an energy condition necessary for fabrication process, wherein an advantage of using the arc as the heat source of the heating system is primarily on the high power and the excellent stability; and further, the technique of arc control system is mature and the cost of establishment of the system is relatively low. After the material immersed in the cooling liquid of the vacuum chamber is excited by the arc-inducing machine to produce the arc, the temperature produced will be high enough to evaporate the material, and the nanoscale metal particle can be obtained through condensation. Due to the nanoparticles directly stored in the liquid, the nanoparticles can be carried with the cooling liquid to an area collection to be classified and selected, and then the dried particles of those can be separated from the liquid-state cooling liquid through the extraction process.

As shown in FIG. 1, the conventional vacuum submerged arc manufacture equipment 1 primarily consists of a vacuum chamber 11, an arc-inducing system 12, a cooling liquid circulatory system 13, and a pressure balance system 14. Wherein the pressure balance system 14 substantially includes a vacuum pump 141 and a switching valve 142, which are used to keep the vacuum chamber 11 under proper vacuum pressure. The deionized water is used as a dielectric liquid in the vacuum chamber 11, wherein the metal bar is located in the bottom, wherein keeps proper gap with the bar of the same material located in the arc-inducing machine 121 in the arc-inducing system 12. The arc-inducing system 12 can provide a stable arc current as the heat source of the heating system, while the arc-inducing system 12 can be used to set or adjust the important process parameters of the desired current, dischargeable time, dischargeable rest time, servo providing time, and dischargeable interval, etc. The cooling circulatory system 13 controls the switch valve 131 to make a cooling liquid 111 inside the vacuum chamber 11 achieving a stable low-temperature state, which is helpful to make crystal grain nucleation, and to simultaneously prevent the growth of the crystal grain; thus, the nanoparticles with smaller diameters and more uniform distribution can be obtained.

The patents or technical theses disclosed related to the above-mentioned on-line sampling technique, analysis technique and relevant process for the nanoparticle fluid or suspension are extremely few, and the more relevant prior patents are as below:

The analysis method and technique of the particle diameter distribution measurement and the solid composition and the concentration in the suspension (U.S. Pat. No. 5,569,844, Oct. 29, 1996): They primarily arrange the probe, sensor, and stirrer within the suspension sample, and use the decay degree from the ultrasonic emission to the received signal to decide the particle diameter inside the suspension, while the measurement scale is around the micrometer level.

Rapid fluid sampler (Taiwan R.O.C. Publication No. 120030 Utility Patent): An oil or fluid sampler, the principle thereof is to use an inlet to introduce the air and an outlet with gradually open downward funnel structure to produce the vacuum suction to proceed the sampling action.

Automatic sampling apparatus (Taiwan R.O.C. Publication No. 248309 Utility Patent): Using the siphon principle is to catch the specimens of the sample trough inside the general chemical examination instrument and rearrange new specimens; and thus the problem derived from manually replacing the sample can be avoided.

Ultrasonic enhanced submerged arc vacuum oscillation nanoparticle manufacture method and machine (R.O.C. Publication No. 506867 Patent): By using the deionized water or the discharge processed liquid as the dielectric liquid under vacuum condition, the material will be melted and evaporated instantly due to the arc discharge, and in the mean time. The disturbance and impact force from the ultrasonic oscillator make the vaporized metal tend to deflect the high-temperature melted region resulting in more uniform and precise particle dimension. Manufacturing method and machine structure for the nanoparticle material vacuum arc enclosure fluid field (Taiwan R.O.C. Patent Application Serial No. 091114909): Its characteristic is to put the original material in the quartz crucible of the vacuum chamber and induce the arc to make the material evaporated, while the cooling liquid of the enclosure fluid field will cool and condense the evaporated material floating from the quartz crucible to produce the nanoscale metal particle material with uniform distribution.

Though there are various characteristics and functions for above-mentioned relevant patents, respectively; however, there are no related patents or documents focusing on the development of the on-line sampling and detection of the nanoparticle vacuum submerged arc process (low temperature and low pressure) neither in domestic country nor in abroad.

The nanoparticle vacuum submerged arc manufacture method and machine (Taiwan R.O.C. Patent Publication No. 434067 is a novel nanoparticle manufacture method around the world, wherein the pressure and the temperature of the deionized water maintains at negative pressure approximately below 100 Torr and the range of 3° C. to 5° C., respectively, during the process. Using off-line TEM to observe the nanoparticle distribution of the Ti nanoparticles or $TiO_2$ nanoparticles produced from pure Ti, and the major diameters of the nanoparticle distribution are within the range of 10~200 nm. Because the process parameters effecting the nanometer generation control are numerous, the particle parameter data obtained from the present off-line particle measurement, undoubtedly, will be influenced by the problems of particle deposition phenomenon, contamination induced by the test handling process, and particle diameter distribution accuracy.

Furthermore, in the view of the optimal requirement for the process, because the amount of the manufacture parameters of the vacuum submerged arc process is plenty, and it's time-consuming for obtaining a set of parameter data, it will take about 2 hours to complete an effective sampling following the present process settings and restrictions; therefore, it is hard to effectively proceed the optimal design work of the process and the system parameters.

SUMMARY OF THE INVENTION

In view of above description, the inventors devote themselves to study based on their relevant research experiences to try to use the principle of the pressure difference between the vacuum bump and the vacuum chamber and the constant temperature design of the sample pipeline; thus the sample can be precisely caught and is able to flow into the predetermined collector. The sample won't be vaporized in the vacuum due to the temperature increase result from ambient temperature; therefore, it is applicable to the relevant nanoparticle fluid process such as various gas or liquid phase nanoparticle manufacture technique and thus the invention comes true. Further, if the invention integrate with the granule analysis apparatus to carry out latest measurement and data analysis of the nanoparticle fluid with latest process characteristics, wherein the nanoparticle fluid is caught from the nanofluid process line, thus, the optimal design work of the process and the system parameters and particle quality monitor may be proceeded efficiently.

Thus, an objective of the invention is to provide an on-line sampling apparatus and sampling method for the metal nanoparticle fluid, thereby the nanoparticle fluid with real time process characteristics can be caught on-line as sample and the efficiency and accuracy for sampling can be enhanced; therefore, the optimal process parameters for manufacture can be rapidly determined. Another objective of the invention is to provide with an on-line sampling apparatus and sampling method, which combines with the granule analysis technique of the metal nanoparticle fluid and can be used as the on-line measurement analysis of the nanoparticles and the optimal control of the process.

To achieve above-mentioned and other objectives, the invention can provide with an on-line sampling apparatus for metal nanoparticle fluid, which combines with a manufacture equipment capable of producing the metal nanoparticle fluid under negative pressure environment and on-line catch the nanoparticle fluid with real time process characteristics as sample, wherein the said sampling apparatus includes:

a collector connecting to the said negative pressure environment of the said manufacture equipment through a constant temperature pipeline, which is used to receive the said sample, and there is a first switch valve provided within the said constant temperature pipeline, a negative pressure generation unit connecting to the said collector, which provides a pressure difference lower than the said negative pressure environment, and there is a second switch valve provided between, and a control unit connecting to the said first and second switch valves to carry out the control of the switch on/off thereof and the sampling control of the said pressure difference. Thus, through the sampling control from the control unit, the nanoparticle fluid with real time process characteristics in the manufacture equipment of the metal nanoparticle fluid can be on-line caught as sample, such that the efficiency and accuracy for sampling can be enhanced, further, it is beneficial to find out optimal process parameters for the manufacture rapidly. Also, the time taken for catching sample and the error and inconvenience for off-line measurement, which are not avoidable for the conventional art can be reduced, and the deposition phenomenon of the nanometer suspension resulting from above delay can also be prevented, therefore, the measurement results of the sample can be ensured to be more representative and accurate.

Furthermore, the invention can also be realized in providing an on-line sampling apparatus for the metal nanoparticle fluid, which combines with a manufacture equipment capable of producing the metal nanoparticle fluid under negative pressure environment and on-line catch the nanoparticle fluid with real time process characteristics as sample, wherein the said sampling apparatus includes:

a collector connecting to the said negative pressure environment of the said manufacture equipment through a constant temperature pipeline, which is used to receive the said sample, and there is a first switch valve provided within the said constant temperature pipeline, a negative pressure generation unit connecting to the said collector, which provides a pressure difference lower than the said negative pressure environment, and there is a second switch valve provided between, a constant dielectric liquid supply unit connecting to the said negative pressure environment of the said manufacture equipment, and a control unit connecting to the said constant dielectric liquid supply unit to carry out the supply control, and connecting to the said first and second switch valves to carry out the control of the switch on/off thereof and the sampling control of the said pressure difference. Thus, through the sampling control from the control unit, the nanoparticle fluid with real time process characteristics in the manufacture equipment of the metal nanoparticle fluid can be on-line caught as sample, such that the efficiency and accuracy for sampling can be enhanced, further, it is beneficial to find out optimal process parameters for the manufacture rapidly. Also, the time taken for catching sample and the error and inconvenience for off-line measurement, which are not avoidable for the conventional art can be reduced, and the deposition phenomenon of the nanometer suspension resulting from above delay can also be prevented, therefore, the measurement results of the sample can be ensured to be more representative and accurate.

In the techniques achieved through above-described two sampling apparatus, besides maintaining the temperature of the pipeline through the design of the constant temperature pipeline, there are heat insulation layers provided on the said collector and outside of the said first switch valve to prevent the sample caught from being vaporized due to ambient temperature increase. Wherein, the said collector consists of an openable vacuum container inside which a sample container is provided, the said constant temperature pipeline connects to the said sample container via the said vacuum container, the said vacuum container consists of a vacuum jar and a cover, and a buckle structure is provided to seal up, the said buckle structure includes a ring and a hook provided on the said vacuum jar and the said cover, respectively, further, the said vacuum container provides with a first channel and a second channel, the said first channel is provided for being passed by the said constant temperature pipeline, and the said second channel is provided for connecting with the said negative pressure generation unit.

The said constant dielectric liquid supply unit at least includes a constant absorber and a switch valve, the said switch valve connects with the said constant absorber, the said negative pressure environment, and a dielectric liquid source, respectively, and the said switch valve connects with the said control unit to control the switch between one of the two states below:

the said constant absorber connects with the said dielectric liquid source and draws constant dielectric liquid, the said constant absorber connects with the said negative pressure environment and draws constant dielectric liquid into the said negative pressure environment.

Wherein, the said constant absorber is comprised of a pump attached on a frame, and a spring established to provide a piston rod of the said pump the automatic constant draw power, the said pump is fixed to the front of the said frame, the said spring is disposed in the middle of the said frame, and the end of the said piston rod of the said pump is restricted by the end of the said spring, thus, the said piston rod can keep constantly the draw power drawn from the said pump, and the distance the said piston rod can draw is restricted by the length of the said frame and become constant.

Above-described sampling apparatus may include a suspension container provided in the said negative environment of the said manufacture equipment, and the said constant temperature pipeline connects to one side of the said suspension container, and an upper electrode and an lower electrode of the said manufacture equipment may be provided on the said suspension container, and another side of the said suspension container provides with a channel for introducing the dielectric liquid. Further, the said sampling apparatus may include a granule analysis equipment connecting to the said collector, thereby the said granule analysis equipment can carry out real time measurement and data analysis for the sample caught, thus the on-line measurement analysis of the nanoparticles and the optimal process control may be accomplished.

The invention further provide an on-line sampling method for metal nanoparticle fluid, which is applicable to a manufacture equipment capable of producing the metal nanoparticle fluid under negative pressure environment, the said sampling method includes:

providing a collector collocating with the heat insulation mechanism and connecting to the said negative pressure environment of the said manufacture equipment to receive the nanoparticle fluid with real time process characteristics as sample, providing the said collector a pressure difference lower than the said negative pressure environment so that the sample can enter the said collector, and providing a control unit to carry out the switch on/off of the said collector and the sampling control of the said pressure difference. Thus, through the sampling control, the nanoparticle fluid with real time process characteristics in the manufacture equipment of the metal nanoparticle fluid can be on-line caught as sample, such that the efficiency and accuracy for sampling can be enhanced, further, it is beneficial to find out optimal process parameters for the manufacture rapidly. Also, the time taken for catching sample and the error and inconvenience for off-line measurement, which are not avoidable for the conventional art can be reduced, and the deposition phenomenon of the nanometer suspension resulting from above delay can also be prevented, therefore, the measurement results of the sample can be ensured to be more representative and accurate.

Furthermore, the invention can also be realized in providing an on-line sampling method for metal nanoparticle fluid, which is applicable to a manufacture equipment capable of producing the metal nanoparticle fluid under negative pressure environment, the said sampling method includes:

providing a constant dielectric liquid supply unit connecting to the said negative pressure environment of the said manufacture equipment to supply constantly the dielectric liquid, providing a collector collocating with the heat insulation mechanism and connecting to the said negative pressure environment of the said manufacture equipment to receive the nanoparticle fluid with real time process characteristics as sample, providing the said collector a pressure difference lower than the said negative pressure environment so that the sample can enter the said collector, and providing a control unit to carry out the supply control of the said constant dielectric liquid supply unit, and carry out the switch on/off of the said collector and the sampling control of the said pressure difference. Thus, through the sampling control, the nanoparticle fluid with real time process characteristics in the manufacture equipment of the metal nanoparticle fluid can be on-line caught as sample, such that the efficiency and accuracy for sampling can be enhanced, further, it is beneficial to find out optimal process parameters for the manufacture rapidly. Also, the time taken for catching sample and the error and inconvenience for off-line measurement, which are not avoidable for the conventional art can be reduced, and the deposition phenomenon of the nanometer suspension resulting from above delay can also be prevented, therefore, the measurement results of the sample can be ensured to be more representative and accurate.

In the techniques achieved through above-described two sampling methods, the said heat insulation mechanism includes wrapping the heat insulation layers outside of the said collector and the pipeline through which the said collector connects to the said negative pressure environment, further, establishing a first switch valve within the connection between the said collector and the said negative pressure environment, the said first switch valve is controlled by the said control unit to switch on/off the said collector, and the outside of the said first switch valve is insulated by the said heat insulation mechanism. Thus, it can prevent the sample caught from being vaporized due to ambient temperature increase.

Further, the said heat insulation mechanism includes providing, for example, a negative pressure generation unit of a vacuum pump, to supply the said pressure difference of the said collector, and providing a second switch valve between the said negative pressure generation unit and the said collector, the said second switch valve is controlled by the said control unit to control the said pressure difference.

Wherein, the said constant dielectric liquid supply unit is comprised of a constant absorber and a switch valve, the said switch valve connects with the said constant absorber, the said negative pressure environment, and a dielectric liquid source, respectively, and the said switch valve connects with the said control unit to control the switch between one of the two states below: the said constant absorber connects with the said dielectric liquid source and draws constant dielectric liquid, the said constant absorber connects with the said negative pressure environment and draws constant dielectric liquid into the said negative pressure environment.

Further, the said heat insulation mechanism includes a constant absorber comprised of a pump attached on a frame, and a spring established to provide a piston rod of the said pump the automatic constant draw power, the said pump is fixed to the front of the said frame, the said spring is disposed in the middle of the said frame, and the end of the said piston rod of the said pump is restricted by the end of the said spring, thus, the said piston rod can keep constantly the draw power drawn from the said pump, and the distance the said piston rod can draw is restricted by the length of the said frame and become constant.

In above-described sampling method, let the said collector connect to a suspension container provided in the said negative environment, and an upper electrode and a lower electrode of the said manufacture equipment may be provided on the said suspension container, and one side of the said suspension container provides with a channel for introducing the dielectric liquid.

Further, an additional granule analysis equipment may connect to the said collector, thereby the said granule analysis equipment can carry out real time measurement and data analysis for the sample caught, thus the on-line measurement analysis of the nanoparticles and the optimal process control may be accomplished.

In addition, it is not essential for above-described granule analysis equipment to directly or indirectly connect to the said collector, the said collector may be moved out of above-mentioned sampling apparatus. The relevant measurement and analysis of the granule or distribution may be achieved through appropriate granule analysis apparatus, which may still meet the requirement of the effective sample characteristics providing with the on-line process characteristics.

DETAILED DESCRIPTION OF THE PREFERRED EMBODIMENTS

Figure 1:
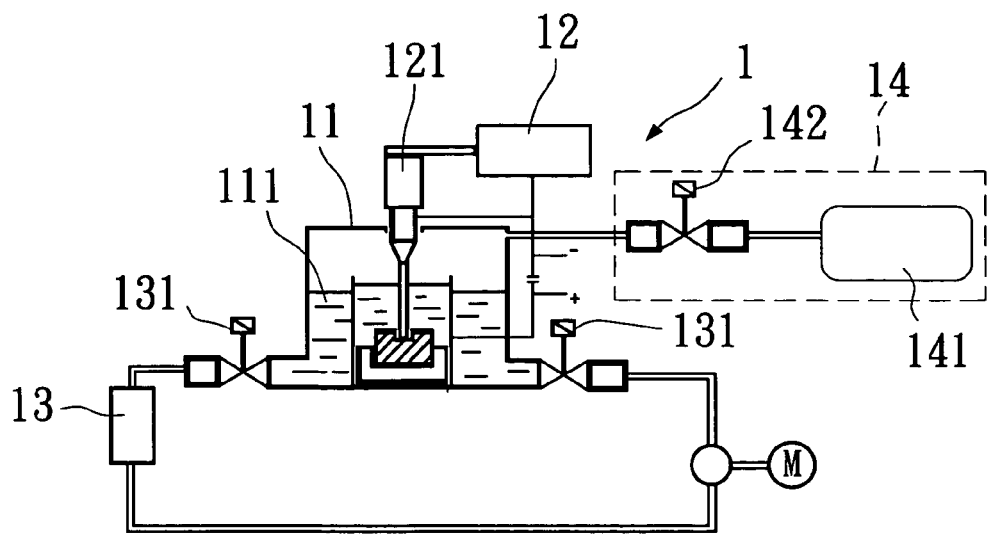
FIG. 1 is the system block diagram of the conventional vacuum submerged manufacture equipment.
Figure 2:
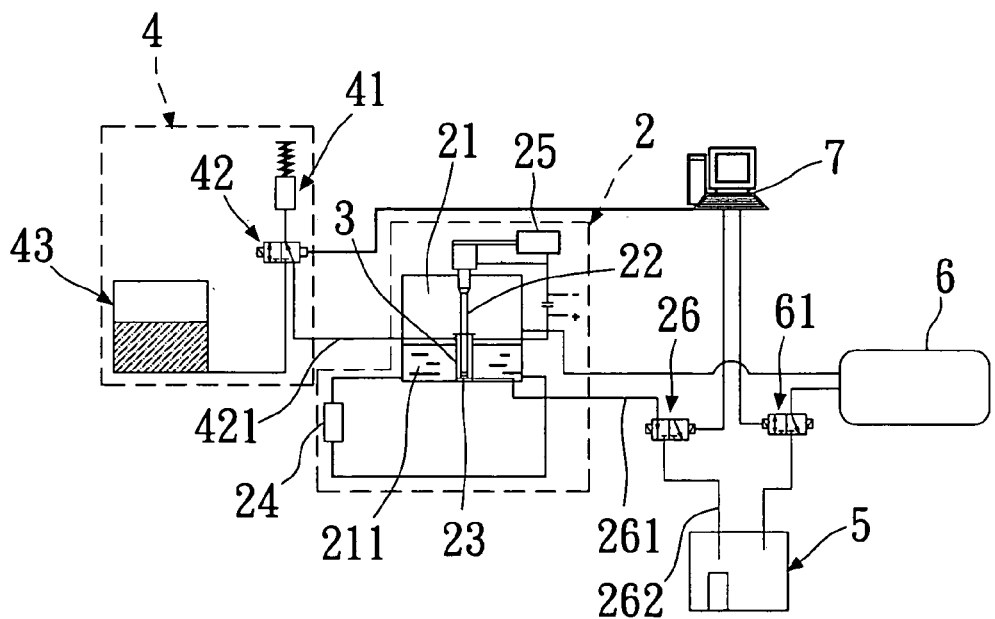
FIG. 2 is the system block diagram of the invention.

To make the examiner understanding the objectives, characteristics and effects of the invention, the invention will be described in detail through the embodiments described below and the accompanied drawings:

Please refer to FIG. 2, which is the system block diagram of the invention. As shown in the figure, the on-line sampling apparatus of the metal nanoparticle fluid of the invention is provided to be integrated into a manufacture equipment 2 which can produce the metal nanoparticle fluid under the negative pressure environment of a vacuum chamber 21, for example, the vacuum submerged arc nanoparticle manufacture machine, to on-line catch the nanoparticle fluid with real time process characteristics as sample. Generally, the manufacture equipment 2 provides with an arc inducing system 25 to provide the heating source, and there is cooling liquid in the vacuum chamber 21, further, there are a cooling liquid circulatory system 24 and a pressure balance system used to keep proper vacuum pressure inside the vacuum chamber 21, due to the manufacture equipment 2 being not the technical focus of the invention, the description about it will be omitted. The sampling equipment includes:

a suspension container 3 provided in the vacuum chamber 21 of the manufacture equipment 2 to produce the nanoparticle fluid with real time process characteristics, and an upper electrode 22 and an lower electrode 23 of the manufacture equipment 2 can be provided thereon, and one side of the suspension container 3 connects to a two-way two position solenoid valve through a constant temperature pipeline 261, and the other side of the suspension container 3 connects to a three way two position solenoid valve through a pipeline 421 to introduce the dielectric liquid, a constant dielectric liquid supply unit 4 used to constantly supply the dielectric liquid to the above-mentioned suspension container 3, which consists of a dielectric liquid-container 43, a three-way-two position solenoid valve 42, and a constant absorber 41, the three way two position solenoid valve 42 connects with the constant absorber 41, the dielectric liquid container 43, and the pipeline 421, respectively, and can be controlled to switch the constant absorber 41 to connect with one of the dielectric liquid container 43 and the suspension container 3 (through the pipeline 421), a collector 5 connecting to a two-way two position solenoid valve 26 through a constant temperature pipeline 262, which can be controlled to switch to connect the above-mentioned suspension container 3 to receive the sample, a vacuum pump 6 connecting to the collector 5 through a two-way two position solenoid valve 61, which can be controlled to provide the collector 5 a pressure difference lower than the vacuum chamber 21, the vacuum pump 6 may be provided additionally, or may be the existing vacuum pump 6 in the original manufacture equipment 2 (originally, to provide the vacuum chamber 21 a proper negative pressure), in the embodiment, the same vacuum pump is employed, a control unit 7 comprised of for example, a control software of the computer built-in mechanical and electrical interface, which connects to the three way two position solenoid valve 42 to carry out the supply control of the dielectric liquid, and connects to the two-way two position solenoid valve 26 and the two-way two position solenoid valve 61 to carry out the switch on/off and the sampling control of the pressure thereof, respectively. In the design of above-mentioned sampling apparatus, the constant temperature pipelines 216, 262 may be PU pipeline wrapped with heat insulation layers, besides, both of the collector 5 and the two-way two position solenoid valve 26 should be provided with heat insulation layers to insulate thereof, thus good heat insulation can be made to prevent the sample from vaporizing due to temperature increase. However, it should be noted that the objective for achieving constant temperature or heat insulation is not limited to provide with above-mentioned heat insulation layers, it can also be achieved by using multi-layer composite insulation, are insulation, constant temperature system or other ways.

Figure 3:
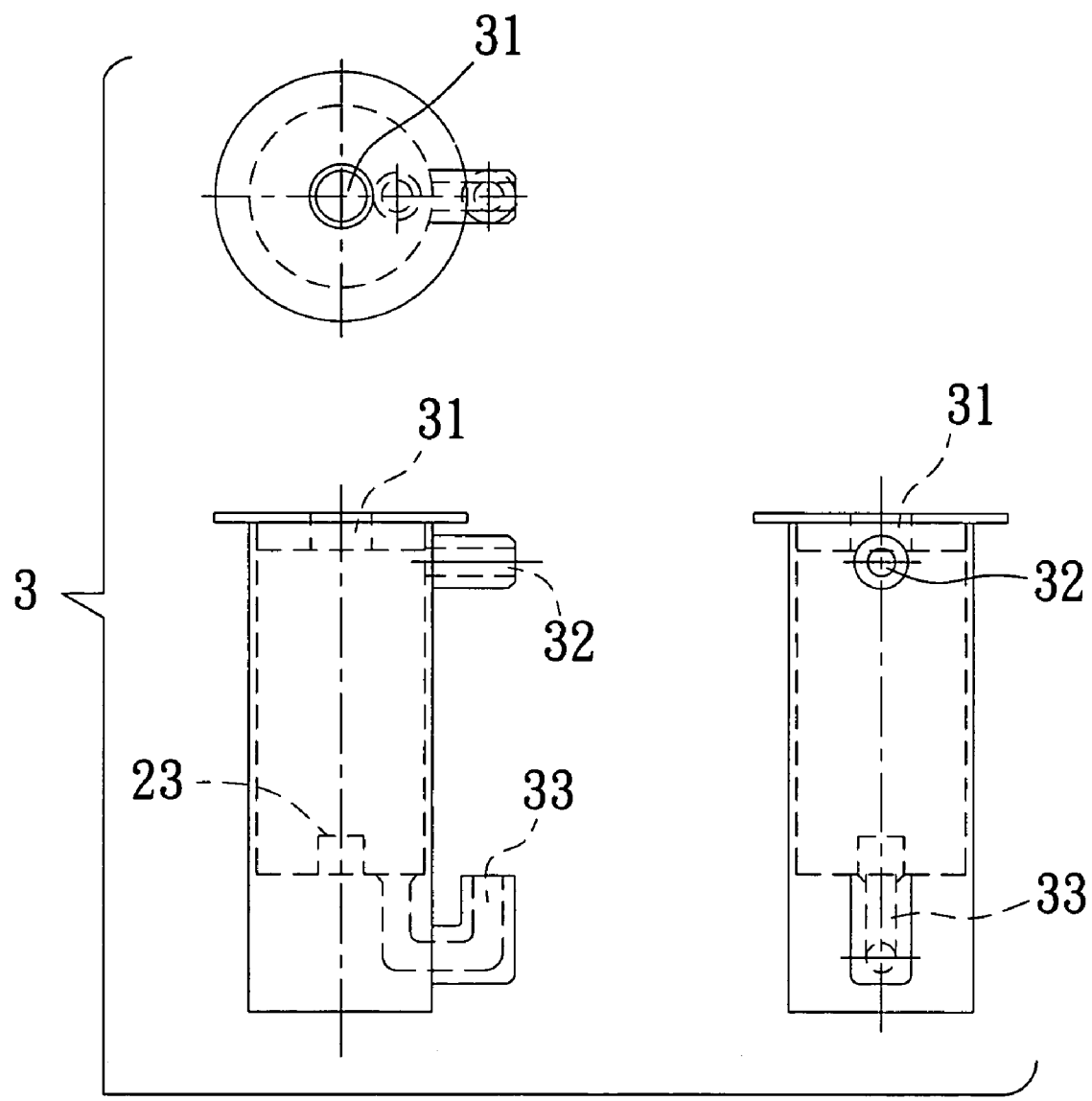
FIG. 3 is the 2D view of the suspension container of the invention.
Figure 4:
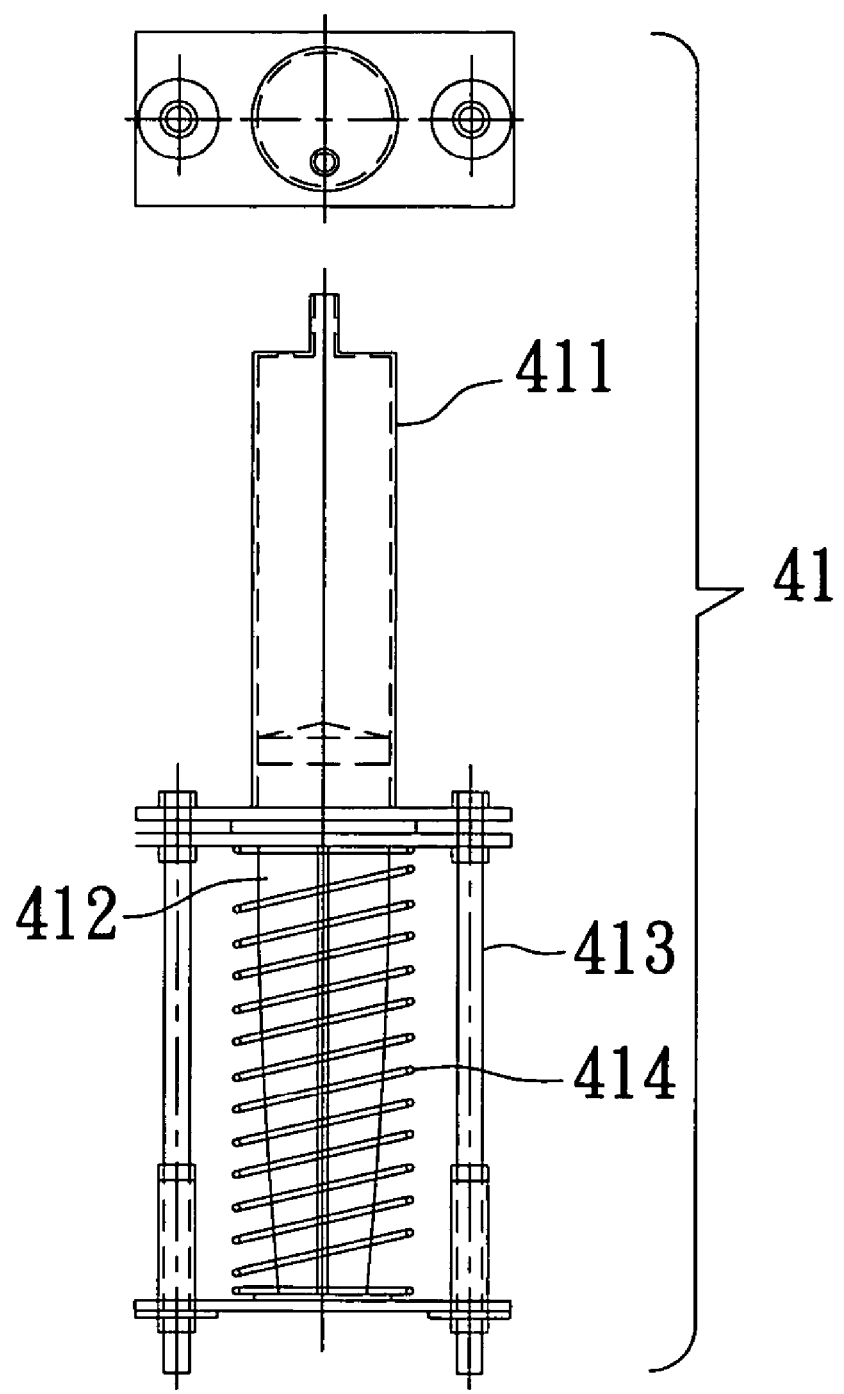
FIG. 4 is the 2D view of the constant absorber of the invention.

Please refer to FIG. 3, which is the 2D view of the suspension container of the invention. As shown in the figure, the suspension container 3 is substantially cylinder structure, the central part of the bottom thereof can be provided with a lower electrode 23 of the manufacture equipment 2, the top thereof is provided with a perforation 31 on which an upper electrode 22 of the manufacture equipment 2 can be provided, there are connectors 32, 33 preserved up and down of one side of the suspension container 3, respectively, to conduct a pipeline 421 and the constant temperature pipeline 261 shown in FIG. 2. The suspension container 3 is provided for injecting sufficient and constant dielectric liquid to make the upper electrode 22 and the lower electrode 23 immerse in the dielectric liquid, thus it advantages in making the nanoparticles produced spread uniformly in the dielectric liquid of the suspension container 3. Please refer to FIG. 4, which is the 2D view of the constant absorber of the invention. As shown in the figure, the constant absorber 41 is comprised of a pump 411 attached on a frame 413, and a compression spring 414 established to provide a piston rod 412 of the pump 411 the automatic constant draw power. Wherein, the pump 411 is fixed to the front of the frame 413, the compression spring 414 is disposed in the middle of the frame 413, and the end of the piston rod 412 of the pump 411 is restricted by the end of the compression spring 414, thus, the piston rod 412 can keep constantly the draw power drawn from the pump 411, and the distance the piston rod 412 can draw is restricted by the length of the frame 413 and become constant. Therefore, the capacity of the pump 411 is fixed via the automatic draw amount of the piston rod 412. While the constant absorber 41 connects to the negative environment of the vacuum chamber 21 as shown in FIG. 2, the piston rod 412 will be compressed and eject the dielectric liquid drawn in the pump 411, and the compression spring will be compressed simultaneously and store the elasticity, on the contrary, while the constant absorber 41 connects to the dielectric liquid container 43, the elasticity of the compression spring 414 will be released and the piston rod 412 will be drawn out automatically to draw constant dielectric liquid into the pump 411. Through the specific structure design of the constant absorber 41, there are three specific advantages obtained as below:

Simplicity in structure, and is easy to maintain and replace,

The capacity (volume) of the dielectric liquid drawn each time is fixed and easy controllable, Not subject to noise interference.

Figure 5:
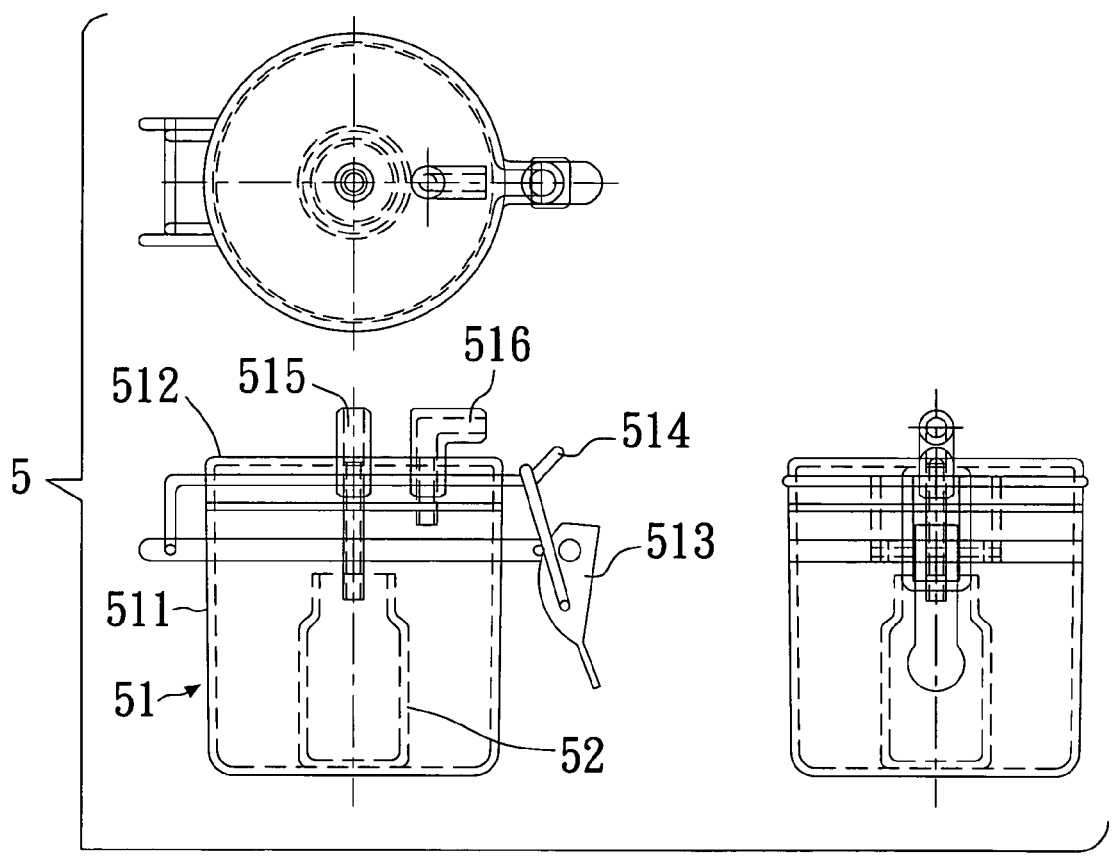
FIG. 5 is the 2D view of the collector of the invention.

Please then refer to FIG. 5, which is the 2D view of the collector of the invention. As shown in the figure, the collector 5 consists of an openable vacuum container 51 inside which a sample container 52 is provided. The vacuum container 51 consists of a vacuum jar 511 and a cover 512, and a buckle structure is provided to seal up, the buckle structure includes a ring 513 and a hook 514 provided on the vacuum jar 511 and the cover 512, respectively. Further, there are a first pipeline connector 515 and a second pipeline connector 516 provided to constitute two channels, wherein the first pipeline connector 515 is provided for being passed by the constant temperature pipeline 262 and connecting to the sample container 52, as shown in FIG. 2, and the second pipeline connector 516 is provided for conducting to the two-way two position solenoid valve 61 to connect with the vacuum pump 6. The flow direction and amount of the dielectric liquid are controlled by the control unit 7, and the dielectric liquid is supplied constantly to the three way two position solenoid valve 42 of the supply unit 4, thus constant dielectric liquid can be supplied properly into the suspension container 3. The stable arc induced by the arc-inducing system 25 of the manufacture equipment 2 is served as heat source which produces high temperature to vaporize the material (mainly for lower electrode 23), and from which the nanoscale metal particles condensed and spread in the dielectric liquid of the suspension container 3, while the cooling liquid 211 supplied from the cooling circulatory system 24 keeps the nanofluid inside the suspension container 3 in stable low temperature condition, which is helpful to crystal grain nucleation, and simultaneously to prevent the growth of the crystal grain, thus, the nanoparticles with smaller diameters and more uniform distribution can be obtained, and the evaporation can be avoided.

Then the switch on/off and the sampling control of pressure difference for the two-way two position solenoid valves 26, 61 are carried out by the control unit 7. When both of the two-way two position solenoid valves 26, 61 switch on, the vacuum degree of the collector 5 caused by the vacuum pump 6 is higher than the one in the vacuum chamber 21, i.e. the collector 5 produces the pressure difference lower than the negative environment of the vacuum chamber 6, resulting that the sample flows automatically from the suspension container 3 to the collector 5 through the constant temperature pipeline 261, 263, and the switch control for the two-way two position solenoid valves 26, 61 can be carried out properly to make the sample enter into and store in the sample container 52.

When there is a particle size analysis apparatus, for example a granule analyzer, which conducts to the collector 5 (or the sample container 52), attached to above-mentioned sampling apparatus, the granule analysis apparatus can carry out real time size distribution measurement and data analysis and output for the sample caught, thereby the efficiency and accuracy can be enhanced, and further it is helpful to find out best process parameters of the manufacture rapidly. And the time taken for catching sample and the errors and inconvenience for off-line measurement, which are not avoidable for the conventional art can be significantly reduced, and the deposition phenomenon of the nanometer suspension resulting from above delay can also be prevented, therefore, the measurement results of the sample can be ensured to be more representative and accurate. Whereas it should be noted that the granule analysis apparatus could be conducted to the collector 5 or the sample container 52 directly or indirectly based on the probe device thereof, for example, to replace the two-way two position solenoid valve 26 with a three way two position solenoid valve to conduct the granule analysis apparatus. Further, it is not essential for the granule analysis apparatus to be conducted to the collector 5 either directly or indirectly, it is also possible to move out the collector 5 from above-mentioned sampling apparatus, and then carry out relevant measurement and analysis for the granule or distribution by proper granule analysis apparatus, thus, the effective sample characteristics with on-line process characteristics can still be achieved.

If above-mentioned granule analysis apparatus is selected as for example an electron microscope, then the operation equipment for practicing dry, load plate transportation to the sample, nanoparticle fluid, should be established additionally between the granule analysis apparatus and the collector 5, resulting from the specific environment of various kinds of granule analysis apparatus. The detailed description for the granule analysis apparatus will be omitted, due to it is not the creation or characteristics of the invention.

The on-line sampling method of the metal nanoparticle fluid of the invention is realized in, for example, above-mentioned sampling apparatus, which is applicable to a manufacture equipment 2 capable of producing the metal nanoparticle fluid under the negative pressure environment of the vacuum chamber 21, the sampling method includes:

providing, for example, above-mentioned constant dielectric liquid supply unit 4 connecting the manufacture equipment 2 to the suspension container 3 of the vacuum chamber 21 to supply constantly the dielectric liquid, providing, for example, above-mentioned collector 5 collocating with the heat insulation mechanism such as heat insulation layer or the other way and connecting to the suspension container 3 of the manufacture equipment 2 to receive the nanoparticle fluid with real time process characteristics as sample, providing the collector 5 a pressure difference lower than above-mentioned vacuum chamber 2 so that the sample can enter the collector 5, and providing, for example, above-mentioned control unit 7 to carry out the supply control of the constant dielectric liquid supply unit 4, and carry out the switch on/off of the collector 5 and the sampling control of the pressure difference. Thus, through the sampling control, the nanoparticle fluid with real time process characteristics in the manufacture equipment 2 of the metal nanoparticle fluid can be on-line caught as sample, such that the efficiency and accuracy for sampling can be enhanced, further, it is beneficial to find out optimal process parameters for the manufacture rapidly. Also, the time taken for catching sample and the error and inconvenience for off-line measurement, which are not avoidable for the conventional art can be reduced, and the deposition phenomenon of the nanometer suspension resulting from above delay can also be prevented, therefore, the measurement results of the sample can be ensured to be more representative and accurate.

In the techniques achieved through above-described sampling method, the heat insulation mechanism includes wrapping the heat insulation layers outside of the collector 5 and the pipeline through which the collector 5 connects to the vacuum chamber, thus, it can prevent the sample caught from being vaporized due to ambient temperature increase.

Further, the heat insulation mechanism includes providing a granule analysis apparatus connecting to the collector 5 to carry out real time measurement and data analysis for the sample caught, thus, it is helpful to achieve on-line measurement analysis of the nanoparticles and optimal control of the process.

In above-mentioned automatic on-line sampling technique of the metal nanoparticle fluid, including the apparatus and the method, the automatic on-line sampling condition for the metal nanoparticle fluid means the sampling parameters of sampling time, dielectric liquid volume, and size of the suspension container, due to the manufacture mechanism characteristics of the vacuum submerged arc process, the situation that the measured values vary with the sampled nanofluid under different sampling conditions will happen. Therefore, in view of the sampling conditions, the granule analysis for the sampled nanoparticle fluid should be carried out under various sampling time and dielectric liquid capacity (volume), in order to regulate proper nanofluid sampling conditions, and further to obtain the nanofluid sample with process characteristics. So the adjustment and control of above-disclosed sampling conditions can be fulfilled through employing the corresponding collocation of the suspension container 3, constant absorber 41, collector 5 and appropriate control of the control unit. Meanwhile, due to the certain range of the proper measurement concentration for general granule analysis apparatus, the amount of the dielectric liquid volume effects the concentration of the nanoparticles in the nanofluid, consequently, it should be noted seriously on the sample for proper sampling time control.

In summary, the invention employs the negative pressure environment of the vacuum to replenish the dielectric liquid, and makes use of the pressure difference to make the sample flow from the vacuum chamber to the collector. Furthermore, the invention achieve automatic sampling of the metal nanoparticle fluid through integration of the automatic sampling apparatus and the vacuum submerged arc manufacture equipment, additionally, it combines with the granule analysis apparatus to achieve the on-line measurement analysis of the nanoparticles and the optimal control of the process, and can be integrated to develop automatic on-line nanoparticle (granule and distribution) measurement and quality monitor system. Therefore, the invention can be described as possessing creativity, advancement, and highly industry utility, and can meet the statutory condition of the inventive patent, so the inventive patent application is filed according to law.

The invention claimed is:

1. An on-line sampling apparatus for the metal nanoparticle fluid, which combines with a manufacture equipment which can produce metal nanoparticle fluid under a negative pressure environment of a vacuum chamber and on-line catch the nanoparticle fluid with real time process characteristics as sample, wherein the said sampling apparatus includes:
    a collector connecting to the said negative pressure environment vacuum chamber of the said manufacture equipment through a constant temperature pipeline, which is used to receive the said sample, and there is a first switch valve provided within the said constant temperature pipeline,
    a negative pressure generation unit connecting to the said collector, which provides a pressure difference lower than the said negative pressure environment vacuum chamber, and there is a second switch valve provided between the negative pressure generation unit and the collector, and
    a control unit connecting to the said first and second switch valves to carry out the control of the switch on/off thereof and the sampling control of the said pressure difference.

2. The sampling apparatus of claim 1, wherein the said constant temperature pipeline is comprised of PU pipeline wrapped with a heat insulation layer.

3. The sampling apparatus of claim 1, wherein the said first switch valve and the said second switch valve are two-way, two position solenoid valves.

4. The sampling apparatus of claim 1, wherein the said negative pressure generation unit is comprised of a vacuum pump.

5. The sampling apparatus of claim 1, wherein the said control unit is comprised of control software of a computer built-in mechanical and electrical interface.

6. The sampling apparatus of claim 1, wherein there are heat insulation layers provided outside of the said collector and the said first switch valve for insulation.

7. The sampling apparatus of claim 1, wherein the said collector consists of an openable vacuum container inside which a sample container is provided, and the said constant temperature pipeline connects to the said sample container via the said vacuum container.

8. The sampling apparatus of claim 7, wherein the said vacuum container consists of a vacuum jar and a cover, and a buckle structure is provided to seal up.

9. The sampling apparatus of claim 8, wherein the said buckle structure includes a ring and a hook provided on the said vacuum jar and the said cover, respectively.

10. The sampling apparatus of claim 7, wherein the said vacuum container provides with a first channel and a second channel, the said first channel is provided for passing a sample by the said constant temperature pipeline, and the said second channel is provided for connecting with the said negative pressure generation unit.

11. The sampling apparatus of claim 10, wherein the said first channel and the said second channel are comprised of a first pipeline connector and a second pipeline connector provided on the cover.

12. The sampling apparatus of claim 1, further includes a suspension container provided in the said negative pressure environment vacuum chamber of the said manufacture equipment, and the said constant temperature pipeline connects to one side of the said suspension container.

13. The sampling apparatus of claim 12, wherein an upper electrode and an lower electrode of the said manufacture equipment can be provided on the said suspension container, and another side of the said suspension container provides with a channel for introducing the dielectric liquid.

14. The sampling apparatus of claim 13, wherein the said granule analysis equipment is selected from one of the granule analyzer and the electron microscope.

15. The sampling apparatus of claim 1, further includes granule analysis equipment connecting to the said collector, thereby the said granule analysis equipment can carry out real time measurement and data analysis for the sample caught.

16. An on-line sampling apparatus for the metal nanoparticle fluid, which combines with a manufacture equipment which can produce metal nanoparticle fluid under a negative pressure environment of a vacuum chamber and on-line catch the nanoparticle fluid with real time process characteristics as sample, wherein the said sampling apparatus includes:
- a collector connecting to the said negative pressure environment vacuum chamber of the said manufacture equipment through a constant temperature pipeline, which is used to receive the said sample, and there is a first switch valve provided within the said constant temperature pipeline,
- a negative pressure generation unit connecting to the said collector, which provides a pressure difference lower than the said negative pressure environment vacuum chamber, and there is a second switch valve provided between the negative pressure generation unit and the collector,
- a constant dielectric liquid supply unit connecting to the said negative pressure environment of the said manufacture equipment, and
- a control unit connecting to the said constant dielectric liquid supply unit to carry out the supply control, and connecting to the said first and second switch valves to carry out the control of the switch on/off thereof and the sampling control of the said pressure difference.

17. The sampling apparatus of claim 16, wherein
the said constant dielectric liquid supply unit is comprised of a constant absorber and a switch valve, the said switch valve connects with the said constant absorber, the said negative pressure environment, and a dielectric liquid source, respectively, and the said switch valve connects with the said control unit to control the switch between one of the two states below:
- the said constant absorber connects with the said dielectric liquid source and draws constant dielectric liquid,
- the said constant absorber connects with the said negative pressure environment and draws constant dielectric liquid into the said negative pressure environment.

18. The sampling apparatus of claim 17, wherein the said switch valve is a three way, two position solenoid valve.

19. The sampling apparatus of claim 17, wherein the said constant absorber is comprised of a pump attached on a frame, and a spring established to provide a piston rod of the said pump the automatic constant draw power.

20. The sampling apparatus of claim 19, wherein the said pump is fixed to the front of the said frame, the said spring is disposed in the middle of the said frame, and the end of the said piston rod of the said pump is restricted by the end of the said spring, thus, the said piston rod can keep constantly the draw power drawn from the said pump, and the distance the said piston rod can draw is restricted by the length of the said frame and become constant.

21. The sampling apparatus of claim 16, wherein the said negative pressure environment of the said manufacture equipment is a vacuum chamber in which a vacuum pump is disposed to balance the said negative pressure environment.

* * * * *